United States Patent
Myerson et al.

(10) Patent No.: US 10,072,261 B1
(45) Date of Patent: Sep. 11, 2018

(54) DOUBLE COUPLING METHOD FOR OLIGONUCLEOTIDE SYNTHESIS

(71) Applicant: Agilent Technologies, Inc., Santa Clara, CA (US)

(72) Inventors: Joel Myerson, Berkeley, CA (US); Siyuan Chen, San Mateo, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/470,779

(22) Filed: Mar. 27, 2017

Related U.S. Application Data

(60) Provisional application No. 62/313,641, filed on Mar. 25, 2016.

(51) Int. Cl.
*C07H 21/00* (2006.01)
*C12N 15/10* (2006.01)
*C12Q 1/6806* (2018.01)

(52) U.S. Cl.
CPC ......... *C12N 15/1093* (2013.01); *C07H 21/00* (2013.01); *C12Q 1/6806* (2013.01)

(58) Field of Classification Search
CPC .............................. C07H 21/00; C12N 15/1093
USPC ............................................ 536/25.3; 506/16
See application file for complete search history.

(56) References Cited

U.S. PATENT DOCUMENTS

| | | | | |
|---|---|---|---|---|
| 5,824,793 A | * | 10/1998 | Hirschbein | C07H 19/10 536/25.3 |
| 2006/0041114 A1 | * | 2/2006 | Sinha | C07D 213/18 536/24.3 |
| 2006/0247431 A1 | * | 11/2006 | Wolter | C07H 21/02 536/25.33 |
| 2016/0229884 A1 | * | 8/2016 | Indermuhle | C07H 1/00 |

OTHER PUBLICATIONS

Leproust, et al., "Synthesis of high-quality libraries of long (150mer) oligonucleotides by a novel depurination controlled process", Nucleic Acids Research, 2010, 38(8): 2522-2540.
Pon, et al., "Prevention of guanine modification and chain cleavage during the solid phase synthesis of oligonucleotides using phosphoramidite derivatives", Nucleic Acids Research, 1986, 14(16): 6453-6470.

\* cited by examiner

*Primary Examiner* — Jezia Riley

(57) ABSTRACT

Aspects of the present disclosure include methods for double coupling a nucleoside phosphoramidite during synthesis of an oligonucleotide. The method can include coupling a free hydroxyl group of a nucleoside residue with a first sample of a protected nucleoside phosphoramidite via an internucleoside P(III) linkage, followed by exposure to an oxidizing agent prior to a second coupling step with a second sample of the protected nucleoside phosphoramidite, and further exposure to an oxidizing agent. The method finds use in synthesizing an oligonucleotide on a solid phase support, such as a planar surface. The double coupling method can be utilized at one or more nucleotide positions during oligonucleotide synthesis thereby reducing single base deletion rates. Oligonucleotide containing compositions synthesized according to the disclosed methods are also provided.

20 Claims, No Drawings

Specification includes a Sequence Listing.

DOUBLE COUPLING METHOD FOR OLIGONUCLEOTIDE SYNTHESIS

CROSS-REFERENCING

This application claims the benefit of U.S. provisional application Ser. No. 62/313,641, filed on Mar. 25, 2016, which application is incorporated by reference herein.

INTRODUCTION

Traditional DNA synthesis consists of 4 steps: phosphoramidite coupling, capping of unreacted hydroxyls, phosphite triester oxidation to phosphate triester, and removal of the terminal dimethoxytrityl-group with acid. Failures of the coupling step, if subsequently successfully capped, result in a ladder of shortmers of all possible lengths (oligonucleotides having n−1, n−2, n−3, etc., lengths compared to n, the desired full-length oligonucleotide sequence). Failure of the capping step, or failure of the detritylation step, result in a larger amount of (n−1)mer, in which the (n−1) impurity is one shorter than the full length. This (n−1)mer length oligonucleotide is not a pure single compound, and consists of single base deletion failures distributed over the entire length of the oligo.

In order to improve the coupling efficiency of traditional phosphoramidite chemistry on solid support such as controlled pore glass using an automated synthesizer a "double couple" cycle is often used. A traditional double coupling cycle is performed before the capping step. The capping step, in turn, is performed before the oxidation step because the capping step is thought to reverse branching side reactions that can occur at the 06 position of guanine nucleobases (Pon R T, Usman N, Damha M J, Ogilvie K K: Prevention of guanine modification and chain cleavage during the solid phase synthesis of oligonucleotides using phosphoramidite derivatives. Nucleic Acids Res 1986, 14(16):6453-6470). The double coupling cycle is performed by repeating the step of addition of activator and phosphoramidite monomer to the detritylated oligonucleotide on the solid support, before capping and oxidation. No oxidation step is performed prior to the second coupling step, otherwise the benefit of reversing the branching during the capping step is lost, because oxidation of the phosphite triester internucleotide linkage stabilizes the undesirable branched oligonucleotide side product.

SUMMARY

Aspects of the present disclosure include methods for double coupling a nucleoside phosphoramidite during synthesis of an oligonucleotide. The method can include coupling a free hydroxyl group of a nucleoside residue with a first sample of a protected nucleoside phosphoramidite via an internucleoside P(III) linkage, followed by exposure to an oxidizing agent prior to a second coupling step with a second sample of the protected nucleoside phosphoramidite, and further exposure to an oxidizing agent. The method finds use in synthesizing an oligonucleotide on a solid phase support, such as a planar support surface that finds use in oligonucleotide arrays. The double coupling method can be utilized at one or more nucleotide positions during oligonucleotide synthesis thereby reducing single base deletion rates. Oligonucleotide containing compositions synthesized according to the disclosed methods are also provided.

DEFINITIONS

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

Following long-standing patent law convention, the terms "a", "an", and "the" refer to "one or more" when used in this application, including the claims. Thus, for example, reference to "a cell" includes a plurality of such cells, and so forth.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The methods described herein include multiple steps. Each step can be performed after a predetermined amount of time has elapsed between steps, as desired. As such, the time between performing each step can be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step can be performed after an incubation or waiting time after completion of the previous step, e.g., a few minutes to an overnight waiting time.

Numeric ranges are inclusive of the numbers defining the range.

The terms "nucleotide" or "nucleotide moiety", as used herein, refer to a sub-unit of a nucleic acid (whether DNA or RNA or analogue thereof), which includes a phosphate group, a sugar group and a heterocyclic base, as well as analogs of such sub-units. Other groups (e.g., protecting groups) can be attached to any component(s) of a nucleotide.

The terms "nucleoside" or "nucleoside moiety", as used herein, refer a nucleic acid subunit including a sugar group and a heterocyclic base, as well as analogs of such sub-units. Other groups (e.g., protecting groups) can be attached to any component(s) of a nucleoside. The "nucleoside residue" refers to a nucleic acid subunit that is linked to a support (e.g., via an optional linker) or linked to a growing oligonucleotide, e.g., that is itself immobilized on a support.

The terms "nucleoside" and "nucleotide" are intended to include those moieties that contain not only the known purine and pyrimidine bases, e.g. adenine (A), thymine (T), cytosine (C), guanine (G), or uracil (U), but also other heterocyclic bases that have been modified. Such modifications include methylated purines or pyrimidines, alkylated purines or pyrimidines, acylated purines or pyrimidines, halogenated purines or pyrimidines, deazapurines, alkylated riboses or other heterocycles. Such modifications include, e.g., diaminopurine and its derivatives, inosine and its derivatives, alkylated purines or pyrimidines, acylated purines or pyrimidines, thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, and substituted phenoxyacetyl, dimethylformamidine, dibutylformamidine, pyrrolodinoamidine, morpholinoamidine, and other amidine derivatives, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 7-deazaadenine, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

A "nucleobase" references the heterocyclic base of a nucleoside or nucleotide. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups including locked nucleic acids (LNA) and unlocked nucleic acids (UNA), 2'-fluoro, 2'-O-alkyl, 2'-O-ethoxymethoxy, or are functionalized as ethers, amines (e.g., 3'-amino), or the like.

The term "analogues", as used herein, refer to molecules having structural features that are recognized in the literature as being mimetics, derivatives, having analogous structures, or other like terms, and include, for example, polynucleotides incorporating non-natural (not usually occurring in nature) nucleotides, unnatural nucleotide mimetics such as 2'-modified nucleosides, peptide nucleic acids, oligomeric nucleoside phosphonates, and any polynucleotide that has added substituent groups, such as protecting groups or linking groups.

The term "nucleic acid", as used herein, refers to a polymer of any length, e.g., greater than about 2 bases, greater than about 10 bases, greater than about 100 bases, greater than about 500 bases, greater than 1,000 bases, up to about 10,000 or more bases composed of nucleotides, e.g., deoxyribonucleotides or ribonucleotides, and may be produced synthetically. Naturally-occurring nucleotides include guanosine and 2'-deoxyguanosine, cytidine and 2'-deoxycytidine, adenosine and 2'-deoxyadenosine, thymidine and uridine (G, dG, C, dC, A, dA, T and U respectively).

A nucleic acid may exist in a single stranded or a double-stranded form. A double stranded nucleic acid has two complementary strands of nucleic acid may be referred to herein as the "first" and "second" strands or some other arbitrary designation. The first and second strands are distinct molecules, and the assignment of a strand as being a first or second strand is arbitrary and does not imply any particular orientation, function or structure. The nucleotide sequences of the first strand of several exemplary mammalian chromosomal regions (e.g., BACs, assemblies, chromosomes, etc.), as well as many pathogens, are known, and may be found in NCBI's Genbank database, for example. The second strand of a region is complementary to that region.

As used herein, the terms "oligonucleotide" and "polynucleotide" are used interchangeably to refer to a single stranded multimer of nucleotides of, inter alia, from about 2 to 1000 nucleotides. Oligonucleotides may be synthetic and, in some embodiments, are 10 to 50 nucleotides in length or 50 to 1000 nucleotides in length. Oligonucleotides may contain ribonucleotide monomers (i.e., may be oligoribonucleotides) or deoxyribonucleotide monomers. Oligonucleotides may contain, 10 to 20, 21 to 30, 31 to 40, 41 to 50, 51-60, 61 to 70, 71 to 80, 80 to 100, 100 to 150, 150 to 500 or greater than 500 nucleotides in length, for example.

The terms "deoxyribonucleic acid" and "DNA", as used herein, refers to a nucleic acid composed of nucleotides and/or deoxyribonucleotides.

The terms "ribonucleic acid" and "RNA", as used herein, refer to a nucleic acid composed of nucleotides and/or ribonucleotides.

An "internucleotide bond" or "internucleotide linkage" refers to a chemical linkage between two nucleoside moieties, such as the phosphodiester linkage in nucleic acids found in nature, or linkages well known from the art of synthesis of nucleic acids and nucleic acid analogues. An internucleotide bond may include, e.g., a phosphate, phosphonate, or phosphite group, and may include linkages where one or more oxygen atoms are either modified with a substituent or a protecting group or replaced with another atom, e.g., a sulfur atom, or the nitrogen atom of a mono- or di-alkyl amino group.

Given the benefit of this disclosure, one of ordinary skill in the art will appreciate that synthetic methods, as described herein, may utilize a variety of protecting groups. The phrase "protecting group", as used herein, refers to a species which prevents a portion of a molecule from undergoing a specific chemical reaction, but which is removable from the molecule following completion of that reaction. A "protecting group" is used in the conventional chemical sense as a group which reversibly renders unreactive a functional group under certain conditions of a desired reaction, as taught, for example, in Greene, et al., "Protective Groups in Organic Synthesis," John Wiley and Sons, Second Edition, 1991. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" binds to a segment of a molecule to prevent any further chemical transformation of that segment during the remaining synthesis process. It should be noted that the functionality protected by the protecting group may or may not be a part of what is referred to as the protecting group.

The terms "hydroxyl protecting group" or "O-protecting group", as used herein, refers to a protecting group where the protected group is a hydroxyl. A "reactive-site hydroxyl" is the terminal 5'-hydroxyl during 3'-5' polynucleotide synthesis, or the 3'-hydroxyl during 5'-3' polynucleotide synthesis. A "free reactive-site hydroxyl" is a reactive-site hydroxyl that is available to react to form an internucleotide bond (e.g., with a phosphoramidite functional group) during polynucleotide synthesis.

A "DNA writer" refers to a device that uses inkjet heads to deliver droplets of phosphoramidite and activator solutions to a substantially smooth, substantially solid support surface to create large numbers of unique sequences of DNA on a small scale. Compared to traditional DNA synthesis, this technology creates 10 million to 10 billion times smaller quantities of DNA than are created using widely available automated chemistry machines using controlled pore glass as the support. Due to these differences in scale and methodology, oligonucleotide synthesis chemistry performed using a DNA writer may behave quite differently than when using traditional automated chemistry machines, and existing literature regarding oligonucleotide synthesis chemistry using traditional automated chemistry machines is often not instructive or predictive about how oligonucleotide synthesis chemistry will behave on a DNA writer.

The term "substantially solid," as used herein for a surface, means that the location(s) on the surface of the support where oligonucleotide synthesis is occurring is resistant to the diffusion, absorption, or permeation of the relevant reagents and chemicals of oligonucleotide synthesis beyond the surface and into the body of the support (in contrast to commercial polymeric oligo synthesizer supports, which permit such diffusion and permeation, such that oligo synthesis occurs in the body of the support).

The term "substantially smooth," as used herein for a surface, means that the location(s) on the surface of the support where the oligonucleotide synthesis is occurring is at most superficially irregular, such that irregularities, if any, are not of a scale which would substantially affect the rapidity with which reagents can be uniformly applied to, mixed on, or removed from the surface (in contrast to commercial "controlled pore glass" oligo synthesizer supports, which contain pores and irregularities that slow the application and removal of reagents).

A substantially solid, substantially smooth surface need not be flat, and would include, for example, flat surfaces, tubes, cylinders, arrays of depressions or wells, and combinations of these elements, as well as other designs presenting surface portions with the above-described attributes. Substantially solid, substantially smooth surfaces are surfaces (or portions of surfaces) that can be addressed by an inkjet print head.

DETAILED DESCRIPTION

As summarized above, the present disclosure provides methods for double coupling a nucleoside phosphoramidite during synthesis of an oligonucleotide. The method can include coupling a free hydroxyl group of a nucleoside residue with a first sample of a protected nucleoside phosphoramidite via an internucleoside P(III) linkage, followed by exposure to an oxidizing agent prior to a second coupling step with a second sample of the protected nucleoside phosphoramidite, and further exposure to an oxidizing agent. The method finds use in synthesizing an oligonucleotide on a solid phase support, such as a planar support surface that finds use in oligonucleotide arrays. The double coupling method can be utilized at one or more nucleotide positions during oligonucleotide synthesis thereby reducing single base deletion rates. Oligonucleotide containing compositions synthesized according to the disclosed methods are also provided.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Methods of Double Coupling

Aspects of the present disclosure include methods for performing a double coupling cycle at one or more nucleotides of a target oligonucleotide sequence during synthesis of the oligonucleotide on a solid support. After the first coupling step, a small percentage (e.g., 0.1 to 1 mol %) of the solid support-bound free terminal groups can remain unreacted, which can lead to base deletions and over the course of an oligonucleotide synthesis, a variety of shortmer sequences (e.g., (n−1)mer sequences). Such non-target sequences can be difficult to remove during purification. The present disclosure provides double coupling methods having a sequence of steps which provide for synthetic oligonucleotide compositions having a reduced amount of shortmer oligonucleotide sequence impurities. The subject method can include a double coupling cycle including two coupling steps of a nucleoside reactant (with an optional oxidation step in between), and an oxidation step after the two coupling steps to oxidize the P(III) internucleoside linkages that are produced to P(V) linkages. In certain instances of the method, no capping step is performed. In some instances, the double coupling cycle can include, sequentially: a first coupling step, a second coupling step, and an oxidation step, without capping before the oxidation step. In certain instances, the double coupling cycle can include, sequentially: a first coupling step, an oxidation step, a second coupling step and an oxidation step. Capping is optional in this embodiment, which can be performed before or after the second oxidation step.

As used herein, the terms "couple" and "coupling" refer to the covalent attachment of a nucleoside monomer or dimer reactant to the free terminal of a nucleoside residue of a growing oligonucleotide according to a desired sequence. Coupling may be achieved via any suitable chemistry which finds use in oligonucleotide synthesis. Coupling chemistries of interest include, but are not limited to, phosphoramidite chemistry. The subject methods can be directed to the preparation of a target oligonucleotide sequence that is a DNA or RNA sequence. As such, in certain instances, the subject methods involve phosphoramidite couplings with a 3'-hydroxyl or 5'-hydroxyl group of a terminal nucleoside or nucleotide residue of a growing oligonucleotide chain, depending on whether the direction of synthesis is performed in the 5' to 3' direction or the in the 3' to 5' direction.

In certain embodiments, the subject methods can be directed to the preparation of a target oligonucleotide sequence that can include one or more phosphoramidate or thiophosphoramidate internucleoside linkages. In certain cases, such linkages can be prepared via phosphoramidite couplings with a 3'-amino group of a terminal nucleoside or nucleotide residue of a growing oligonucleotide chain.

The nucleoside residue may have a variety of terminal functional groups to which an incoming nucleoside monomer or dimer reactant may be coupled, depending on the type of coupling chemistry utilized, the direction of synthesis and whether the oligonucleotide includes conventional ribose and/or deoxyribose sugars or modified sugar moieties that find use in preparation of oligonucleotide analogs. The free terminal group of the nucleoside residue can be located at a variety of positions, e.g., the 3' or 5' positions of a ribose or deoxyribose sugar moiety, and can include a variety of functional groups, e.g., hydroxyl, amino or thiol, connected via an optional linker, e.g., to the sugar moiety.

In some instances, coupling includes reaction of a free terminal hydroxyl group (e.g., a 5'-hydroxyl or a 3'-hydroxyl) with a nucleoside phosphoramidite to produce a phosphoramidite internucleoside linkage.

In some instances, coupling includes reaction of a free terminal amino group (e.g., a 3'amino) with a nucleoside phosphoramidite to produce an internucleoside linkage, such as a N3'→P5' phosphoramidite internucleoside linkage. The N3'→P5' phosphoramidite internucleoside linkage can then be subsequently oxidized to a N3'→P5' phosphoramidate internucleoside linkage, or sulfurized to a N3'→P5' thiophosphoramidate internucleoside linkage, using any suitable methods.

In some embodiments, the method includes contacting a free terminal group (e.g., a terminal hydroxyl or amino group) of a nucleoside residue attached to a solid phase support with a first sample of a protected nucleoside phosphoramidite to couple the nucleoside monomer to the terminal nucleoside residue via an internucleoside P(III) linkage. In certain cases, the free terminal group is a 5'-hydroxyl group of the nucleoside residue. In certain cases, the free terminal group is a 3'-hydroxyl group of the nucleoside residue. In certain cases, the free terminal group is a 5'-amino group of the nucleoside residue. In certain cases, the free terminal group is a 3'-amino group of the nucleoside residue.

Oxidation of the internucleotide linkages may be performed using any suitable methods. As used herein, the terms "oxidize," "oxidation," "oxidizing", and the like, in reference to a phosphorus-containing internucleosidic linkage means a process or treatment for converting the phosphorus atom of the linkage from a phosphorus (III) form to a phosphorus (V) form. In certain embodiments, the method further includes, after the first coupling step, exposing the contacted nucleoside residue to an oxidizing agent to oxidize the linkage and produce a first coupled and oxidized product.

Aspects of the present disclosure include a double coupling procedure where no capping step is performed prior to oxidation. In some cases, no capping step is performed during the synthesis cycle. In some cases, a capping step is performed after all oxidation steps have been performed and before deprotection. In certain instances, the method optionally includes a capping step before or after the final oxidation step. As used herein, "capping" refers to a step involving reacting any residual free terminal groups of the growing oligonucleotide that remain unreacted with incoming nucleotide reactant after coupling.

Aspects of the present disclosure include removal of the reagents from the first coupling before the addition of the reagents for the second coupling. This can be done by introducing a wash step in between the two coupling steps, or by performing an oxidation step in between the two coupling steps, followed by a wash step. In the latter, the oxidation reagents can both remove the reagents from the first coupling and oxidize the phosphorus from the P(III) to the P(V) state. The wash step after the oxidation step serves to remove the oxidation reagents and prepare the oligonucleotide for the second coupling step.

The steps of the subject methods described herein include a washing step performed after the first coupling step and before the second coupling step. The washing step can be preceded by an oxidation step. Any suitable solvents, acids, bases, salts, other additives and combinations thereof can be utilized in wash solutions that find use in the subject methods. In some instances, the subject method includes the following steps: first coupling, oxidation, washing, second coupling, oxidation. In some instances, the subject method includes the following steps: first coupling, washing, second coupling, oxidation with no capping step. In some instances, the subject method includes the following steps: first coupling, washing, second coupling, washing, oxidation with no capping step. In some instances, the subject method includes the following steps: first coupling, washing, oxidation, washing, second coupling, oxidation. In some instances, the subject method includes the following steps: first coupling, washing, oxidation, washing, second coupling, washing, oxidation. In some instances, the subject method includes the following steps: first coupling, washing, second coupling, oxidation, followed by capping. In some instances, the subject method includes the following steps: first coupling, washing, second coupling, washing, oxidation, followed by capping.

In some embodiments, the subject methods include one or more washing steps. In certain cases, after each oxidation step, the solid support to which the growing oligonucleotide is attached is washed with a suitable solvent. In certain cases of the subject methods where no oxidation step is performed between the first and second couplings of a double couple cycle, the solid support to which the growing oligonucleotide is attached is washed with a suitable solvent after the first coupling step. In certain cases, after each deprotection step (e.g., detritylation), the solid support to which the growing oligonucleotide is attached is washed with a suitable solvent. In certain instances, the solvent used in the one or more washing steps is acetonitrile.

The nucleoside residue can be attached to any suitable solid support, e.g., as described in greater detail herein. As used herein, the term "attached" means a nucleoside residue is bound or linked to a solid support, directly or indirectly, via a covalent bond or a non-covalent interaction. In certain instances, a nucleoside residue is attached to a solid phase support via a growing oligonucleotide chain and a linker that is covalently bonded to the support.

In some instances, the subject double coupling method is performed using a nucleoside residue attached to a support that is substantially solid. In some cases, the support is a substantially smooth surface. In some cases, the support is a substantially smooth and substantially solid surface. The support may be planar. Any suitable supports that find use in oligonucleotide arrays can be adapted for use in the subject double coupling methods.

Any suitable protecting groups can be utilized to protect the terminal group of the incoming monomer or dimer nucleoside reactant during coupling. Any suitable hydroxyl, amino or thiol protecting groups can be utilized. In some instances, the subject method further includes deprotecting the protected hydroxyl groups of the terminal nucleoside residue that is formed as a product of the coupling. After deprotection, a free terminal group is exposed to which further protected nucleoside monomer or dimer reactants may be coupled as needed.

Methods of Oligonucleotide Synthesis

Aspects of the present disclosure include methods of oligonucleotide synthesis that include the subject double coupling method, e.g., as described herein. In certain instances, the method is performed to prepare an oligonucleotide attached to a solid support that is a substantially solid, substantially smooth surface (e.g., a smooth planar surface).

Any suitable coupling chemistry, coupling reagents and methods may be utilized in the subject methods. Considerable guidance in making selections concerning coupling conditions, protecting groups, solid phase supports, linking groups, deprotection reagents, reagents to cleave products from solid phase supports, purification of product, and the like, in the context of the subject methods can be found in literature, e.g. Gait, editor, Oligonucleotide Synthesis: A Practical Approach (IRL Press, Oxford, 1984); Amarnath and Broom, Chemical Reviews, Vol. 77, pgs. 183-217 (1977); Pon et al, Biotechniques, Vol. 6, pgs. 768-775 (1988); Ohtsuka et al, Nucleic Acids Research, Vol. 10, pgs. 6553-6570 (1982); Eckstein, editor Oligonucleotides. and Analogues: A Practical Approach (IRL Press, Oxford, 1991), Greene and Wuts "Protective Groups in Organic Synthesis", Third edition, Wiley, New York 1999, Narang, editor, Synthesis and Applications of DNA and RNA (Academic Press, New York, 1987), Beaucage and Iyer, Tetrahedron 48: 2223-2311 (1992), and like references.

The coupling step of the subject methods may be carried out in any suitable temperature range. In some instances, the reaction is carried out at ambient temperature (about 15-30 degrees Celsius). The reaction may be performed by adding a solution of the phosphoramidite dimer or monomer and a solution of an activator (or a solution containing the phosphoramidite dimer or monomer and the activator) to the reaction chamber containing the free hydroxyl group of an (oligo)nucleotide covalently attached to a solid support. Generally, activators of interest include nucleophilic catalysts that displace the more stable phosphoramidite amino group to form a highly reactive (and less stable) intermediate which, in turn, reacts with the free 5' hydroxyl group of a solid supported oligonucleotide The monomer (or dimer) and the activator can be premixed, mixed in the valve-block of a suitable synthesizer, mixed in a pre-activation vessel and pre-equilibrated if desired, or they can be added separately to the reaction chamber.

Activators of interest that may be utilized in the subject methods include, but are not limited to, 5-(benzylthio) tetrazole, tetrazole, 5-(ethylthio)tetrazole, 5-(4-nitrophenyl) tetrazole, 5-(2-thiophene) tetrazole, triazole, pyridinium chloride, and the like, e.g. activating agents as described by Beaucage and Iyer Tetrahedron 48: 2223-2311 (1992); Berner et al, Nucleic Acids Research, 17: 853-864 (1989); Benson, Chem. Rev. 41: 1-61 (1947). As used herein, the term "tetrazole activator" refers to activators which are tetrazole or derivatives of tetrazole. In some embodiments, the activator is tetrazole. Convenient solvents include, but are not limited to, propylene carbonate, acetonitrile, tetrahydrofuran, methylene chloride, and the like, and mixtures thereof.

Any suitable protecting group strategies, e.g., protecting group strategies of oligonucleotide synthesis methods, can be adopted for use in the subject methods. For example, when the nucleoside residues include naturally occurring nucleobases, nucleobase protecting groups such as acyl protecting groups (e.g., isobutyryl or benzoyl) or amidine-type protecting groups (e.g., N,N-dialkylformamidinyl) can be utilized to prevent undesirable side reactions.

Any suitable protecting groups can be utilized to protect the terminal group of the incoming monomer or dimer nucleoside reactant during coupling. In certain instances, the terminal group is a hydroxyl, an amino or a thiol group and the protecting group is an acid-labile protecting group such as a triarylmethyl protecting group (e.g., DMT (4,4'-dimethoxytriphenylmethyl)) or a BOC carbamate (tert-butoxycarbonyl), or a base-labile protecting group, such as a FMOC (fluorenylmethyloxycarbonyl). In some instances, the subject method further includes deprotecting the protected hydroxyl group of the terminal nucleoside residue attached to the solid phase support to produce free hydroxy groups; and repeating the synthesis cycle until the target oligonucleotide sequence is synthesized.

Oxidation of the internucleotide linkages may be performed using any suitable methods. Oxidizing agents which are useful in the subject methods include, but are not limited to, iodine, chlorine, bromine, peracids such as m-chlorobenzoic acid, hydroperoxides such as t-butylhydroperoxide, ethyl hydroperoxide, methyl hydroperoxide and the like, 10-camphorsulfonyl)-oxaziridine, ozone, mixed acyl-sulfinic anhydrides such as 3H-2,1-benzoxathiolan-3-one-1-oxide, salts of persulfates such as sodium, ammonium, and tetrabutylammonium persulfate and the like, monoperoxysulfates such as Oxone™, sodium and/or other hypochlorites, peroxides such as diethyl peroxide or bis(trimethylsilyl)peroxide, or hydrogen peroxide or non-aqueous hydrogen peroxide equivalents such as urea/hydrogen peroxide complex, etc. In some cases oxidation reagents may be dissolved in aqueous solutions, such as iodine dissolved in a mixture of water, tetrahydrofuran and pyridine. In some cases oxidation reagents may be dissolved in anhydrous organic solvents, such as 10-camphorsulfonyl)-oxaziridine dissolved in anhydrous acetonitrile. Other useful oxidizing agents which may be used to convert phosphorus (III) to phosphorus (V) are described in Beaucage and Iyer Tetrahedron 48: 2223-2311 (1992).

In some instances, oxidizing an internucleoside linkage includes sulfurization to produce a thio-containing P(V) linkage (e.g., a thiophosphoramidate or thiophosphate linkage). Sulfurization may be performed using any convenient methods. Sulfurization methods of interest include those described by Gryaznov et al., WO2001018015, the disclosure of which is herein incorporated by reference in its entirety. Sulfurizing agents for use in the invention include elemental sulfur, thiuram disulfides such as tetraethyl thiuram disulfide, acyl disulfides such as phenacyldisulfide, phosphinothioyl disulfides such as S-Tetra™, and 1,1-dioxo-3H-1,2-benzodithiol-3-one. In some embodiments, sulfurization may be performed using elemental sulfur (S8). In certain embodiments, sulfurization may be performed using Beaucage reagent, using methods as described by Iyer et al., J. Organic Chemistry 55:4693-4699, 1990.

Any suitable capping reagents may be utilized to cap the free terminal groups. In general, during conventional oligonucleotide synthesis, a small percentage (e.g., 0.1 to 1%) of the solid support-bound free terminal groups (e.g., 5'-OH groups) remains unreacted and needs to be permanently blocked from further chain elongation to prevent the formation of oligonucleotides with an internal base deletion commonly referred to as (n–1) shortmers. In some cases, capping includes acetylation using a capping mixture (e.g., acetic anhydride and 4-dimethylaminopyridine or 1-methylimidazole). Any suitable capping reagents can be utilized. Capping reagents useful in the subject methods include electrophilic reagents such as acetic anhydride and the like, and phosphoramidites, such as diethyleneglycol ethyl ether (2-cyanoethyl)-(N,N-diisopropyl)-phosphoramidite in conjunction with an activator and followed by oxidation.

In certain embodiments, for 3'-to-5' synthesis, a support-bound nucleoside residue is provided having the following structure:

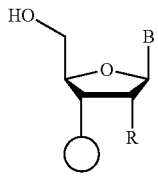

wherein:

represents the solid support (connected via an optional linker) or a support-bound oligonucleotide chain;

R is hydrogen, protected hydroxyl group, fluoro, an alkoxy, O-ethyleneoxyalkyl (O—CH$_2$CH$_2$OR), a protected amino, a protected amido, or protected alkylamino wherein when R is hydrogen, the support-bound nucleoside is a deoxyribonucleoside, as will be present in DNA synthesis, and when R is a protected hydroxyl group, the support-bound nucleoside is a ribonucleoside, as will be present in RNA synthesis; and B is a nucleobase or a protected nucleobase, e.g. a purine or pyrimidine base.

In certain embodiments, the nucleobase may be a conventional purine or pyrimidine base, e.g., adenine (A), thymine (T), cytosine (C), guanine (G) or uracil (U), or a protected form thereof, e.g., wherein the base is protected with a protecting group such as acetyl, difluoroacetyl, trifluoroacetyl, isobutyryl, benzoyl, N,N-dimethylformamidine, N,N-dimethylacetamidine, N,N-dibutylformamidine, or the like. The purine or pyrimidine base may also be an analog of the foregoing; suitable analogs include, but are not limited to: 1-methyladenine, 2-methyladenine, $N^6$-methyladenine, $N^6$-isopentyladenine, 2-methylthio-$N^6$-isopentyladenine, N,N-dimethyladenine, 8-bromoadenine, 7-deazaadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 7-deazaguanine, 7-deaza-8-azaguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In some embodiments, synthesis of oligonucleotides includes repeating the subject double coupling method twice or more during synthesis, such as 30 times or more, 40 times or more, 50 times or more, 60 times or more, 70 times or more, 80 times or more, 90 times or more, 100 times or more, 150 times or more, 200 times or more, or even 300 times or more. In certain embodiments, the double coupling method described herein is performed at every coupling step in the sequence.

In another aspect, the present disclosure provides a method for synthesizing a DNA. In certain embodiments, the synthesized nucleic acid (e.g., a DNA) has a sequence of 30 nucleotides or more, such as 40 nucleotides or more, 50 nucleotides or more, 60 nucleotides or more, 70 nucleotides or more, 80 nucleotides or more, 90 nucleotides or more, 100 nucleotides or more, 125 nucleotides or more, 150 nucleotides or more, 175 nucleotides or more, 200 nucleotides or more, 300 nucleotides or more, or 500 nucleotides or more. In certain embodiments, the synthesized nucleic acid is 1000 nucleotides or less in length. In some instances, in any one of the embodiments described above, the synthesized nucleic acid (e.g., a DNA) has a sequence having 1000 nucleotides or less, such as 500 nucleotides or less, 400 nucleotides or less, or 300 nucleotides or less. In certain embodiments, the synthesized DNA has a sequence of between about 30 and about 500 nucleotides, such as between about 30 and about 200 nucleotides, between about 30 and about 100 nucleotides, between about 40 and about 100 nucleotides, between about 40 and about 80 nucleotides, between about 50 and about 70 nucleotides, or between about 55 and about 65 nucleotides. In certain embodiments, the synthesized DNA has a sequence of between about 70 and about 200 nucleotides, such as between about 80 and about 200 nucleotides, between about 90 and about 200 nucleotides, between about 100 and about 200 nucleotides, between about 120 and about 200 nucleotides, or between about 150 and about 200 nucleotides. In certain embodiments, the synthesized DNA has a sequence of between about 50 and about 500 nucleotides, such as between about 100 and about 400 nucleotides, between about 150 and about 300 nucleotides, or between about 200 and about 300 nucleotides. In certain embodiments, the synthesized DNA is of a length of about 200-mer to about 1,000-mer, (e.g., containing, from about 200-mer to about 800-mer, from about 200-mer to about 500-mer, from about 300-mer to about 800-mer, from about 300-mer to about 500-mer).

In certain embodiments, the synthesized oligonucleotide has a reduced error rate in comparison to a conventional method of synthesis (e.g., as described herein), such as an error rate that is reduced to 50% or less, 40% or less, 30% or less, 20% or less, 10% or less, or 5% or less, of that achieved using a control method (for example, if the error rate using a control method is 1 error in 400 nucleotides, a reduction to 10% or less results in 1 error in 4000 or more nucleotides). In some embodiments, the oligonucleotide synthesized according to the subject method includes fewer single nucleotide deletions per 100 nucleotides than is achieved using a control method. In certain embodiments, the oligonucleotide synthesized according to the subject method gives an overall single base deletion rate of 1 in 500, or better ("better" in this context means fewer than 1 single base deletion in 500 nucleotides), such as 1 in 600 or better, 1 in 700 or better, 1 in 800 or better, 1 in 900 or better, 1 in 1000 or better, 1 in 1250 or better, 1 in 1750 or better, 1 in 2000 or better, 1 in 2250 or better, 1 in 2500 or better, 1 in 2750 or better, 1 in 3000 or better, 1 in 3250 or better, 1 in 3500 or better, 1 in 3750 or better, or 1 in 4000 or better. Any suitable methods can be utilized in determining the error rate. Methods of interest include those described by Hecker K H, and R L Rill (1998 Error analysis of chemically synthesized polynucleotides. BioTechniques 24: 256-260).

The method may further comprise calculating the overall cycle yield of an oligonucleotide synthesis reaction, where the term "overall cycle yield" refers to the percentage of n+1 products relative to the amount of n+1 product (a product to which a nucleotide has been added) and n+0 product (a product to which a nucleotide not been added) made during each cycle of a synthesis reaction. The cycle yield can be obtained using the equation:

Cycle yield=$(F/(M+F))^{1/C}$

Where

F=amount of full length oligonucleotide

M=total amount of oligonucleotides having a reduced length as compared to the desired sequence (e.g. n−1, n−2, n−3, etc)

C=number of cycles

In another embodiment, the method may further comprise calculating the single base deletion rate of an oligonucleotide synthesis reaction. The term "single base deletion rate" refers to the rate at which an oligonucleotide synthesis reaction fails to add a monomer, expressed in a per nucleotide basis.

If no capping is performed, the single base deletion rate can be calculated from the cycle yield using the equation:

Single base deletion rate=1/(1-cycle yield)

which results in a calculated single base deletion rate of 1 in X. This means that on average, one out of every X nucleotides synthesized will be missing. For example, if no capping is performed, an oligonucleotide synthesis reaction that has an overall cycle yield of 99% has a single base deletion rate of 1 in 100.

Aspects of the present disclosure further include the nucleic acid products of the subject methods. The nucleic acid products, e.g., RNA, DNA, of the methods of the disclosure may vary in size, ranging in certain embodiments from 30 or more monomeric units in length, such as 50 or more, 100 or more, 150 or more, 200 or more, 250 or more, 300 or more, 350 or more, 400 or more, 450 or more, 500 or more, or even more. In some instances, the nucleic acids are 1000 nucleotides or less in length. In some embodiments, the nucleic acid products are 100 to 1000 monomeric units in length, including, inter alia, 100 to 500 monomeric units in length, such as 200 to 400 or 300 to 500 monomeric units in length, In certain embodiments, the nucleic acid product has a reduced error rate as described above.

The synthetic methods of the present disclosure may be conducted on any suitable solid support having a surface to which chemical entities may bind. In some embodiments, oligonucleotides being synthesized are attached to a support directly or indirectly. The support may optionally be placed in an array of wells or channels. Suitable solid supports may have a variety of forms and compositions and derive from naturally occurring materials, naturally occurring materials that have been synthetically modified, or synthetic materials. In some instances, the support surface is substantially solid. In some cases, the support surface is substantially smooth. In some cases the support surface is substantially solid and substantially smooth. Any suitable supports that find use in oligonucleotide arrays or are used for creating libraries of oligonucleotides on a surface using an inkjet printhead can be adapted for use in the subject methods and compositions. In some cases, the support has a planar surface. In some cases, the planar supports further include a surface layer, e.g., a polymeric matrix or monolayer connected to the underlying support material that includes a density of functional groups suitable for oligonucleotide attachment.

In some cases, a "substantially smooth surface" is a planar surface. The attributes of a substantially solid, substantially smooth surface are a function of the surface itself regardless of the underlying structure supporting the surface and regardless of the shape of the surface. A solid, smooth surface need not be flat or planar, and would include for example, flat surfaces, tubes, cylinders, arrays of depressions or wells, combinations of these elements, as well as other designs presenting surface portions with the above described attributes. In some instances, the solid support includes an array of wells. In some instances, the solid support is configured to include a microarray of oligonucleotides.

In certain embodiments, the surface of the support where the oligonucleotide synthesis occurs should be sufficiently regular to permit surface application of reagents applied by an inkjet. The substantially solid, substantially smooth surfaces (or portions thereof) can be addressed by an inkjet printhead, in which various reagents involved in phosphoramidite oligonucleotide synthesis chemistry can be applied to particular locations on the surface.

Examples of substantially solid and substantially smooth surfaces include, without being limited to, glass, fused silica, silicon dioxide, and silicon. The surfaces may be chemically derivatized while still being substantially solid and substantially smooth (such as described in U.S. Pat. No. 6,444,268, the disclosure of which is herein incorporated by reference in its entirety with respect to surface derivatization)). In contrast, controlled pore glass has extensive pores and is not a substantially solid and substantially smooth surface.

Suitable solid supports are in some cases polymeric, and may have a variety of forms and compositions and derive from naturally occurring materials, naturally occurring materials that have been synthetically modified, or synthetic materials. Examples of suitable support materials include, but are not limited to, polysaccharides such as agarose (e.g., that available commercially as Sepharose®, from Pharmacia) and dextran (e.g., those available commercially under the tradenames Sephadex® and Sephacryl®, also from Pharmacia), polyacrylamides, polystyrenes, polyvinyl alcohols, copolymers of hydroxyethyl methacrylate and methyl methacrylate, silicas, teflons, glasses, and the like.

The initial monomer of the polynucleotide to be synthesized on the support surface is in some cases bound to a linking moiety which is in turn bound to a surface hydrophilic group, e.g., to a surface hydroxyl moiety present on the support. In some cases the polynucleotide is synthesized on a cleavable linker. In some cases the cleavable linker is synthesized at the end of a polynucleotide stilt, which in turn is bound to a surface hydrophilic group, e.g., to a surface hydroxyl moiety present on the support. In certain embodiments of the method said method further comprises cleaving the oligonucleotide from the solid support to produce a free oligonucleotide (e.g., a free nucleic acid). Examples of suitable support materials include, but are not limited to, silicas, silicon and silicon oxide (including any materials used in semiconductor fabrication), teflons, glasses, polysaccharides such as agarose (e.g., Sepharose® from Pharmacia) and dextran (e.g., Sephadex® and Sephacryl®, also from Pharmacia), polyacrylamides, polystyrenes, polyvinyl alcohols, copolymers of hydroxyethyl methacrylate and methyl methacrylate, and the like. In some cases, the initial monomer of the oligonucleotide to be synthesized on the support surface is bound to a linking moiety which is in turn bound to a surface hydrophilic group, e.g., a surface hydroxyl moiety present on a silica support. In some embodiments, a universal linker is used. In some other embodiments, the initial monomer is reacted directly with, e.g., a surface hydroxyl moiety.

In some embodiments, multiple oligonucleotides being synthesized are attached, directly or indirectly, to the same substantially solid, substantially smooth support and may form part of an array. An "array" is a collection of separate molecules of known monomeric sequence each arranged in a spatially defined and a physically addressable manner, such that the location of each sequence is known. The number of locations, or "features," that can be contained on an array will largely be determined by the area of the support, the size of a feature and the spacing between features, wherein the array surface may or may not comprise a local background region represented by non-feature area. Arrays can have densities of up to several hundred thousand or more features per $cm^2$, such as 2,500 to 200,000 features/$cm^2$. The features may or may not be covalently bonded to the support. An "array" includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. An array is "addressable" when it has multiple regions of different moieties (e.g., different polynucleotide sequences) such that a region (i.e., a "feature" or "spot" of the array) at a particular predetermined location (i.e., an "address") on the array will comprises a known predetermined polynucleotide sequence. In some instances, the addressable array will hybridize to a particular target or class of targets (although a feature may incidentally bind non-targets of that feature). Array features are typically, but need not be, separated by intervening spaces.

The solid support comprising an array may be substantially planar or may comprise a plurality of microstructures, such as wells, channels and microchannels, elevated columns or posts. In some embodiments, the array is part of a microfluidic device, and is two or three-dimensional.

In some embodiments, an array of nucleic acids is synthesized by the method and compositions of the present disclosure. Oligonucleotide synthesis on an array can be performed using any suitable methods, where at least one of the couplings performed at a position of the array is a double coupling according to the subject methods. As such, an array of oligonucleotides can be prepared via double coupling a plurality of protected nucleoside phosphoramidites to a plurality of nucleoside residues located at their respective positions of a substantially solid, substantially smooth support surface according to the subject method (e.g., as described herein). It is understood that the steps of array synthesis can be performed in parallel (e.g., where a first step is performed at multiple positions of the array, before a second step is performed at those positions).

In some embodiments, the nucleic acids are kept attached to the array for their use in array-based applications (such as for example gene expression, cytogenetics, genotyping, transcripts or exons profiling etc.). In other embodiments, the nucleic acids are all—or sometime only a subset—released from the substantially solid, substantially smooth support to produce a library or libraries of nucleic acids, or pools that can be optionally amplified prior to or after cleavage from the support. Pools or libraries of nucleic acids can be used for example as baits for selective target enrichment, or used as probes for in situ hybridization assays (e.g. oligonucleotide FISH) or other hybridization assays, multiplex site-directed mutagenesis, multiplex genome engineering and accelerated evolution (MAGE), genes knockout with libraries encoding siRNAs, shRNAs, miRNAs, genome engineering with libraries of nucleic acids encoding CRISPR RNAs and/or Cas proteins, or assembled and ligated into longer DNA fragments, genes and/or genome. In some embodiments, the assembled nucleic acids are DNA having a length from about from about 100 nucleotides to about 5000 nucleotides, such as from about 500 nucleotides to about 1500 nucleotides. In other embodiments, the length of the assembled nucleic acids may vary in size, ranging in certain embodiments from 300 or more nucleotides in length, such as 500 or more, 600 or more, 700 or more, 800 or more, 900 or more, 1000 or more, or 5000 or more nucleotides.

Also provided is a library of nucleic acids produced using the subject compositions and methods. In some embodiments of the library, the library includes a plurality of nucleic acids, where each nucleic acid is synthesized by a subject method as described herein. Also provided is a library including a plurality of nucleic acids having a length from about 300 to about 10,000 nucleotides, wherein each nucleic acid is composed of assembled nucleic acid fragments synthesized by a subject method as described herein. The nucleic acids may be free nucleic acids. The plurality of nucleic acids may have sequences that together define a gene of interest. The plurality of nucleic acids of the library may be assembled into a gene or fragment of a gene, e.g., using any suitable methods of fragment coupling.

The product nucleic acids find use in a variety of applications, including research, diagnostic and therapeutic applications. For example, the product nucleic acids find use in research applications such as genomics, cytogenetics, target enrichment and sequencing, site-directed mutagenesis, synthetic biology, gene synthesis, gene assembly, e.g., as probes, primers, gene fragments, DNA/RNA arrays, libraries of nucleic acids. With respect to diagnostic applications, such as genomics, cytogenetics, oncology, infectious diseases, non-invasive prenatal testing (NWT), target enrichment and sequencing, the product nucleic acids may also find use as probes (for example oligoFISH), primers, gene fragments, transcripts, DNA/RNA arrays, libraries of nucleic acids, libraries of transcripts or other agents employed in diagnostic protocols. With respect to therapeutic applications, the product nucleic acids find use as any DNA, RNA or other nucleic acid therapeutic, such as antisense nucleic acids, in gene therapy applications, gene editing, interfering RNA (i.e., iRNA or RNAi) applications, etc.

Oligonucleotide containing compositions synthesized according to the disclosed methods are also provided. In some cases, the composition includes a population of chemically synthesized oligonucleotides containing fewer than 1 single base deletion in 500 nucleotides as compared to the desired sequence. In certain embodiments, the oligonucleotide compositions contain fewer than 1 in 600, 1 in 700, 1 in 800, 1 in 900, 1 in 1000, 1 in 1250, 1 in 1750, 1 in 2000, 1 in 2250, etc., single base deletion as compared to the desired sequence. In certain instances, the composition comprises a plurality of chemically synthesized oligonucleotides, wherein the oligonucleotides collectively contain fewer than 1 in 1250 single base deletions as compared to the desired oligonucleotide sequence of the plurality of chemically synthesized oligonucleotides.

EXAMPLES

Example 1

The capping step is sometimes left out in the production of DNA microarrays (LeProust E M, Peck B J, Spirin K, McCuen H B, Moore B, Namsaraev E, Caruthers M H: Synthesis of high-quality libraries of long (150mer) oligonucleotides by a novel depurination controlled process. Nucleic Acids Res 2010, 38(8):2522-2540) with the result that coupling and detritylation failures are both exhibited as increased amounts of (n−1)mer, and to a lesser extent, (n−2), (n−3), etc., as would be predicted by a binomial distribution. In such cases, oligonucleotide libraries that are prepared using a single coupling step and cleaved off of the surface of microarrays show single base deletion rates as high as about 1 in 350 to 1 in 300 or worse. Coupling efficiency is affected by, among other factors, both concentration and the relative amount of phosphoramidite used. In some cases, a 3 to 30 fold excess of phosphoramidite over oligonucleotide is used during coupling, e.g., in some cases when synthesizing on a controlled pore glass. With a DNA writer, printing on a substantially solid and substantially smooth surface, the molar excess of phosphoramidite used relative to the oligonucleotides present in a single feature on the microarray is on the order of 25,000×. Under such conditions, it was expected that the reaction is not limited by phosphoramidite, and that double coupling will not help. However, surprisingly, it was discovered that even though there is a very large excess of phosphoramidite present relative to the 5'-hydroxyl oligonucleotide during the coupling step, the single base deletion rate can be improved by performing a second coupling step. The second coupling step can be done after a wash step. The second coupling can be done after an oxidation step. The second coupling can be done after a wash step with no previous oxidation step, and where the second coupling is not followed by a capping step. The second coupling can be done after a wash step with no previous oxidation step, and where the second coupling is followed by an oxidation step, then a capping step.

Any method of double coupling described here can be performed using a DNA writer on a substantially solid and substantially smooth support.

A. Error Rate Determined by Sequencing.

An Agilent DNA writer was used to print a short stilt at the 3'-end comprising 7 dT nucleotides and a cleavable linker, followed by the 150mer oligo below. The synthesis was performed on a glass slide derivatized according to U.S. Pat. No. 6,444,268

(SEQ ID NO: 1)
5'-ATCGCACCAGCGTGT_TGCACATGAAGTATTTATCCACCTGTTTTAT

TTTCATGAAGTTCTTAGACTAGCTGAATTTGTCTTTAAAATATTTGTGCA

AAGCTATTAATATACACATTTTGTAAAAAAAAAAAAAAA_CACTGCGGCT

CCTCA-3'

The 15mer segments at the 5' and 3' ends, shown separated by an underscore, were used as primers for PCR amplification, leaving 120 nucleotides for sequencing determination of single base deletions.

Three conditions were used for synthesizing the 150mer:
1. Normal single coupling.
   a. Couple
   b. Wash with oxidation solution
   c. Wash with acetonitrile
   d. Normal detritylation and wash.
2. Double couple with oxidation between coupling step
   a. 1st Couple
   b. Wash with oxidation solution
   c. Wash with acetonitrile
   d. 2nd couple
   e. Wash with oxidation solution
   f. Wash with acetonitrile
   g. Normal detritylation and wash.
3. Double couple with no oxidation between coupling steps
   a. 1st Couple
   b. Wash with acetonitrile
   c. 2nd couple
   d. Wash with oxidation solution
   e. Wash with acetonitrile
   f. Normal detritylation and wash.

| Experiment 1 (110817). Deletion rates were determined by cloning and sequencing | |
|---|---|
| Condition 1 Single couple control | 1 in 316 single base deletion rate (from 88 clones) |
| Condition 2 Double couple with oxidation | 1 in 1660 single base deletion rate (from 83 clones) |
| Condition 3 Double couple with no oxidation gave very little full length material | |

| Experiment 2 (120514). Deletion rates were determined by cloning and sequencing | |
|---|---|
| Condition 1 Single couple control | 1 in 328 single base deletion rate (from 82 clones) |
| Condition 2 Double couple with oxidation | 1 in 2256 single base deletion rate (from 94 clones) |
| Condition 3 Double couple with no oxidation gave slightly less full length material than with oxidation. | |

B. Error Rate Determined by HPLC

An Agilent DNA writer was used to print a 30mer oligo using the 3 conditions described in section A. The oligo was cleaved off of the surface.

Cycle yields and single base deletion error rates were obtained by determining the amount of full length material and the amount of oligonucleotides having a reduced length. In this example, the performance of the DNA writer was degraded for reasons unrelated to the double coupling, but the double coupling experiments still showed a significant improvement in the single base deletion rate.

| Experiment 3 (160212). Deletion rates were determined by HPLC | |
|---|---|
| Condition 1 Single couple control | 1 in 201 single base deletion rate |
| Condition 2 Double couple with oxidation | 1 in 556 single base deletion rate |
| Condition 3 Double couple with no oxidation. | 1 in 333 single base deletion rate |

EXEMPLARY EMBODIMENTS

Notwithstanding the appended claims, the disclosure set forth herein also contemplates, for example, the following embodiments.

1. A method for synthesizing an oligonucleotide comprising: performing a double coupling cycle at one or more nucleotides of the oligonucleotide sequence during synthesis, wherein the double coupling cycle comprises a first coupling step and a second coupling step, on a substantially solid and substantially smooth surface.

2. The method of clause 1, wherein the double coupling cycle comprises an oxidation step between the first and second coupling steps.

3. A method for synthesizing an oligonucleotide comprising: performing a double coupling cycle at one or more nucleotides of the oligonucleotide sequence during synthesis, wherein the double coupling cycle comprises a first coupling step and a second coupling step, with an oxidation step between the first and second coupling steps, but no capping before the oxidation step.

4. The method of clause 3 performed on a substantially solid and substantially smooth surface.

5. The method of any preceding clauses, wherein a double coupling cycle is performed at all nucleotides of the oligonucleotide sequence during synthesis.

6. A method of producing an array of oligonucleotide features according to the method of any preceding embodiment, wherein at least one double coupling cycle is performed on at least one oligonucleotide feature during synthesis.

7. The method of clause 6, wherein a double coupling cycle is performed at each nucleotide of the oligonucleotide sequence of each oligonucleotide feature during synthesis.

8. The method of any preceding clauses, wherein phosphoramidite coupling chemistry is utilized to synthesize the oligonucleotide sequence.

9. The method of any preceding embodiment, wherein the oligonucleotide sequence is between about 50 and 1000 nucleotides in length.

10. The method of any preceding clause, wherein oligonucleotides of 50-200 nucleotides in length are synthesized with an overall error rate of less than 1 in 500 oligonucleotides.

11. The method of clause 10, wherein the error rate is less than 1 in 600, 1 in 700, 1 in 800, 1 in 900, 1 in 1000, 1 in 1250, 1 in 1750, 1 in 2000, or 1 in 2250 oligonucleotides.

12. A composition comprising a plurality of chemically synthesized oligonucleotides, wherein the oligonucleotides collectively contain fewer than 1 in 1250 single base deletions as compared to the desired oligonucleotide sequence of the plurality of chemically synthesized oligonucleotides.

13. The composition of clause 12, wherein the population of chemically synthesized oligonucleotides contain fewer than 1 in 600, 1 in 700, 1 in 800, 1 in 900, 1 in 1000, 1 in 1250, 1 in 1750, 1 in 2000, 1 in 2250, etc., single base deletion as compared to the desired sequence.

14. The composition of clause 12 or 13, wherein the composition is an array of oligonucleotide features, wherein each feature comprises a population of oligonucleotides that contains fewer than 1 in 1250 single base deletions as compared to compared to the desired oligonucleotide sequence of the oligonucleotide feature.

15. The composition of any one of clauses 12 to 14, wherein the desired oligonucleotide sequence is between about 50 and 1000 nucleotides in length.

16. A method of synthesizing an array of oligonucleotides, the method comprising:
   (a) double coupling a first protected nucleoside phosphoramidite to a first nucleoside residue located at a first position of a planar solid phase support (e.g., as described herein, e.g., according to the method of any one of clauses 1-11 or claims 1-11);
   (b) repeating step (a) at a plurality of locations on the planar solid phase support.

17. The method of clause 16, further comprising: deprotecting the protected hydroxyl groups of the terminal nucleoside residues attached to the plurality of locations of the planar solid phase support to produce free hydroxy groups; and repeating steps (a) through (b) until the array of oligonucleotides is synthesized.

18. A composition comprising a plurality of chemically synthesized oligonucleotides, wherein the oligonucleotides contain fewer than 1 in 1250 single base deletions as compared to the desired oligonucleotide sequence of the plurality of chemically synthesized oligonucleotides.

19. The composition of clause 19, wherein the composition is an array of oligonucleotide features, wherein each feature comprises an oligonucleotide containing fewer than 1 single base deletion in 1250 nucleotides.

20. The composition of any one of clauses 18-19, wherein the oligonucleotides comprise sequences of between about 50 and 1000 nucleotides in length.

21. The composition of any one of clauses 18-20, wherein the plurality of chemically synthesized oligonucleotides define a library of oligonucleotides capable of assembly into a gene or gene fragment.

Additional Exemplary Embodiments

A1. A method for covalently adding a nucleotide to a terminal nucleoside residue attached to a solid support, comprising a double coupling cycle that comprises:
   (a) contacting the terminal nucleoside residue with a first sample of nucleoside phosphoramidite under conditions to couple the nucleoside phosphoramidite to the terminal nucleoside residue via an internucleoside linkage;
   (b) repeating (a) with a second sample of nucleoside phosphoramidite; and
   (c) oxidizing the internucleoside linkage.

A2. The method of A1, further comprising oxidizing the internucleoside linkage after (a) and before (b).

A3. The method of A2, further comprising adding a capping agent after (c), or between (b) and (c).

A4. The method of A1 or A2, wherein no capping is performed.

A5. The method of any of the preceding embodiments, further comprising a washing step between (a) and (b).

A6. The method of any of the preceding embodiments, further comprising a washing step after (b) and before (c).

A7. The method of any of the preceding embodiments, wherein the solid support comprises a substantially solid, substantially smooth surface.

A8. The method of any of the preceding embodiments, wherein the solid support is planar.

A9. The method of any of the preceding embodiments, wherein an error of single base deletion occurs in one or less than one in 500 nucleotides.

A10. The method of any of the preceding embodiments, wherein an error of single base deletion occurs in one or less than one in 1000 nucleotides.

A11. The method of any of the preceding embodiments, wherein an error of single base deletion occurs in one or less than one in 1250 nucleotides.

A12. The method of any of the preceding embodiments, wherein an error of single base deletion occurs in one or less than one in 2000 nucleotides.

A13. The method of any of the preceding embodiments, wherein an error of single base deletion occurs in one or less than one in 3000 nucleotides.

A14. The method of any of the preceding embodiments, wherein an error of single base deletion occurs in one or less than one in 4000 nucleotides.

A15. An array of oligonucleotides prepared using the method of any of the preceding embodiments.

A16. A library of oligonucleotides prepared by cleaving the oligonucleotides from the array of A15.

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended embodiments.

What is claimed is:

1. A method for double coupling a nucleoside phosphoramidite during synthesis of an oligonucleotide, the method comprising:
    (a) contacting a free hydroxyl group of a terminal nucleoside residue attached to a solid phase support with a first sample of a protected nucleoside phosphoramidite to couple the protected nucleoside to the terminal nucleoside residue via an internucleoside P(III) linkage;
    (b) after step (a), exposing the contacted nucleoside residue to an oxidizing agent to oxidize the linkage and produce a first coupled and oxidized product;
    (c) after step (b), contacting the first coupled and oxidized product with a second sample of the protected nucleoside phosphoramidite to couple the protected nucleoside to residual free hydroxyl groups of the terminal nucleoside residue via an internucleoside P(III) linkage; and
    (d) after step (c), adding an oxidizing agent to oxidize the linkage and produce a protected terminal nucleoside residue.

2. The method of claim 1, further comprising:
    (e) deprotecting the protected hydroxyl group of the terminal nucleoside residue to produce a free hydroxyl group;
    (f) repeating steps (a) through (e) until the oligonucleotide is synthesized.

3. The method of claim 1, wherein steps (b) and (d) comprise washing the solid phase support after exposure to the oxidizing agent.

4. The method of claim 1, wherein the solid phase support comprises a substantially smooth and substantially solid surface.

5. The method of claim 1, wherein the solid phase support comprises an array of wells.

6. The method of claim 1, wherein the protected nucleoside phosphoramidite is a nucleoside monomer.

7. The method of claim 1, wherein the protected nucleoside phosphoramidite is a nucleoside dimer.

8. The method of claim 1, wherein synthesis of the oligonucleotide is performed in the 3' to 5' direction.

9. The method of claim 1, wherein synthesis of the oligonucleotide is performed in the 5' to 3' direction.

10. The method of claim 1, wherein no capping is performed.

11. The method of claim 1, wherein oxidizing the linkage produces a phosphotriester linkage.

12. A method of synthesizing an array of oligonucleotides by using the method according to claim 1.

13. The method of claim 12, further comprising:
deprotecting the protected hydroxyl groups of the terminal nucleoside residues attached to the plurality of locations of the solid phase support to produce free hydroxy groups;
repeating the double coupling and deprotection steps until the array of oligonucleotides is synthesized.

14. The method of claim 12, wherein the array comprises oligonucleotides of between about 30 and 1000 nucleotides in length.

15. The method of claim 14, wherein the oligonucleotides are synthesized with an overall single base deletion rate of 1 in 500 or better.

16. The method of claim 1, wherein no capping is performed before step (d).

17. The method of claim 1, wherein no capping is performed after step (d).

18. The method of claim 1, further comprising capping between step (c) and step (d), or after step (d).

19. The method of claim 13, wherein the solid phase support comprises a substantially smooth and substantially solid surface.

20. The method of claim 19, wherein the solid phase support comprises a planar surface.

* * * * *

```
                         SEQUENCE LISTING

<160> NUMBER OF SEQ ID NOS: 1

<210> SEQ ID NO 1
<211> LENGTH: 150
<212> TYPE: DNA
<213> ORGANISM: artificial sequence
<220> FEATURE:
<223> OTHER INFORMATION: synthetic oligonucleotide

<400> SEQUENCE: 1
atcgcaccag cgtgttgcac atgaagtatt tatccacctg ttttattttc atgaagttct      60
tagactagct gaatttgtct ttaaaatatt tgtgcaaagc tattaatata cacattttgt     120
aaaaaaaaaa aaaaacactg cggctcctca                                      150
```